United States Patent [19]

Ma

[11] 4,306,083
[45] Dec. 15, 1981

[54] MULTIPHASE OXIDATION OF ALCOHOL TO ALDEHYDE

[75] Inventor: King W. Ma, Houston, Tex.

[73] Assignee: The Dow Chemical Company, Midland, Mich.

[21] Appl. No.: 150,017

[22] Filed: May 15, 1980

Related U.S. Application Data

[63] Continuation-in-part of Ser. No. 46,899, Jun. 8, 1979, abandoned, which is a continuation-in-part of Ser. No. 953,062, Oct. 19, 1978, abandoned.

[51] Int. Cl.³ ............................................. C07C 45/38
[52] U.S. Cl. .................................. 568/432; 568/431; 568/424
[58] Field of Search ....................... 568/431, 432, 424

[56] References Cited

U.S. PATENT DOCUMENTS 4,119,671 10/1978 Baver et al. ...................... 568/432

Primary Examiner—Bernard Helfin
Attorney, Agent, or Firm—Joyce P. Hill; Douglas N. Deline

[57] ABSTRACT

In a two-phase liquid medium comprising an aqueous alkaline solution and an organic solvent, molecular oxygen and a noble metal-containing catalyst can be used to oxidize aryl-substituted alcohols of the formula $AR(-CH=CH-)_nCH_2OH$ wherein n is 0, 1 or 2, to the corresponding aldehydes. More specifically, the oxidation of an aromatic alcohol, such as p-methoxybenzyl alcohol, can be efficiently carried out in a multiphase system comprising a 5 percent palladium-on-charcoal catalyst, an organic solvent such as methylene chloride, in contact with an aqueous sodium hydroxide solution, in the presence of air or oxygen with good agitation followed by separation of the two phases, recovery of the aldehyde product from the organic solvent and recycle of the aqueous phase without neutralization.

10 Claims, No Drawings

MULTIPHASE OXIDATION OF ALCOHOL TO ALDEHYDE

CROSS REFERENCE TO RELATED APPLICATION

This application is a continuation-in-part of copending Application Ser. No. 046,899, filed June 8, 1979 which was a continuation-in-part of Application Ser. No. 953,062 filed Oct. 19, 1978, both now abandoned.

BACKGROUND OF THE INVENTION

Heyns, K. and L. Blazejewicz, *Tetrahedron*, Vol. 9 (1960) pp. 67–75, report the oxidation of primary aryl-substituted alcohols with air in the presence of platinum deposited on charcoal, or platinum dioxide. Heyns et al., supra, teach that the oxidation of primary aryl-substituted alcohols, such as benzyl alcohol, with oxygen in the presence of a platinum catalyst gives an aldehyde when the operation is carried out in a purely organic medium, while in an aqueous medium the oxidation proceeds as far as the corresponding carboxylic acid. Thus, in the case of benzyl alcohol, oxidation in an n-heptane medium gives benzaldehyde, while in an aqueous medium and in the presence of a little sodium hydroxide, benzoic acid is obtained almost quantitatively.

It is also known that hydroxybenzyl alcohols can be oxidized with oxygen in good yield to the corresponding hydroxybenzaldehyde if palladium is used as the catalyst (Marchand et al., U.S. Pat. No. 3,321,526 "Production of Hydroxybenzaldehydes", May 23, 1967).

The substantially identical catalytic activities of palladium and platinum have been demonstrated (*Methoden der Organischen Chemie*, 4th ed., Houben-Weyl, Vol. 4, Part 2, (1954) pp. 165–193; Dibella, E. P., U.S. Pat. No. 3,673,257, "Process for the Production of Aromatic Hydroxyaldehydes", June 27, 1972). The use of either of these noble metal catalysts results in rapid and almost complete absorption of oxygen. Palladium has been preferred because it selectively limits the oxidation to the aldehyde stage without any appreciable formation of the acid (Marchand et al., supra, column 1, lines 70–72).

In addition to the use of the noble metal catalyst it is observed that nearly all processes for the oxidation of hydroxy aryl-substituted alcohols to the corresponding aldehydes include the addition of caustic or a suitable alkaline agent. The caustic treatment eventually necessitates a neutralization step for the isolation of the desired product; this neutralization step also produces an undesirable brine waste stream.

It is desirable to produce hydroxy aryl-substituted alcohols efficiently and in good yield without the neutralization step that produces an undesirable waste stream. This can now be achieved by the process of this invention wherein aryl-substituted alcohols are oxidized in a multiphase system using an alkaline agent such as caustic in an aqueous solution, an organic liquid which is a solvent for the aldehyde formed, and a noble metal catalyst. This system permits the recycling of the caustic solution without neutralization and allows an efficient work-up and isolation of the desirable aldehyde product from the organic phase.

SUMMARY OF THE INVENTION

Aryl-substituted alcohols of the formula:

Ar(—CH=CH—)$_n$CH$_2$OH wherein n is 0, 1 or 2, can be readily and efficiently converted to the corresponding aldehydes by contacting the aryl-substituted alcohols with an oxygen-containing gas in a multiphase system comprising a noble metal catalyst, an organic solvent and an aqueous alkaline medium. The use of a multiphase system for the oxidation reaction permits recycling of the caustic solution, allows efficient work-up and isolation of the aldehyde product from the organic phase and thereby eliminates the neutralization step which produces an environmentally deleterious waste stream.

DETAILED DESCRIPTION OF THE INVENTION

Aryl-substituted alcohols are oxidized to the corresponding aldehydes with an oxygen-containing gas in a multiphase system comprising a noble metal catalyst, and an organic solvent in contact with an aqueous alkaline medium. The aryl-substituted alcohols that may be oxidized by this process may be represented by the structural formula:

Ar(—CH=CH—)$_n$CH$_2$OH wherein n is 0, 1 or 2 and the hydroxyalkyl- or hydroxyalkenyl-radical is attached to an aromatic compound having at least one benzene ring. The ring structure may be further substituted by substituents selected from halogen, phenyl, alkyl of up to 22 carbon atoms, and alkoxy of up to 22 carbon atoms.

The process of this invention is of particular value in the oxidation of benzyl alcohols that may be represented by the structural formula:

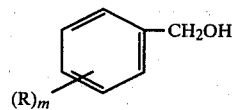

in which the —CH$_2$OH radical is in the ortho-, meta- or para-position relative to R, R is OR', vinyl, nitro, halo, alkyl of 1 to 22 carbon atoms, alkenyl of 1 to 22 carbon atoms, R' is hydrogen, aryl, alkyl of 1 to 22 carbon atoms, and m is a whole number from 0 to 2; when m is 2, the R groups may be the same or different. Illustrative of these compounds are:
benzyl alcohol;
o-hydroxybenzyl alcohol;
m-hydroxybenzyl alcohol;
p-hydroxybenzyl alcohol;
2-hydroxy-4-methylbenzyl alcohol;
2-hydroxy-5-butylbenzyl alcohol;
2-hydroxy-6-methoxybenzyl alcohol;
2-hydroxy-4-ethoxybenzyl alcohol;
3-hydroxy-5-methoxybenzyl alcohol;
3-hydroxy-6-methylbenzyl alcohol;
3-methyl-4-hydroxybenzyl alcohol;
2-butoxy-4-hydroxybenzyl alcohol;
o-vinylbenzyl alcohol and isomers;
p-nitrobenzyl alcohol and isomers;
m-chlorobenzyl alcohol and isomers;
3-phenyl-2-propen-1-ol;
3-anthryl-2-propen-1-ol;
3-(1-naphthyl)2-propen-1-ol;

5-phenyl-2,4-pentadien-1-ol;
5-(1-naphthyl)-2,4-pentadien-1-ol;
5-(1-anthryl)-2,4-pentadien-1-ol;
(hydroxymethyl)naphthalene;
(hydroxymethyl)anthracene;
o-, m-, p-phenyloxybenzyl alcohol;
bis(phenyloxy)benzyl alcohol;
diethoxybenzyl alcohol;
vinyloxybenzyl alcohol;
divinylbenzyl alcohol;
diethylbenzyl alcohol;
ar-nitro-ar-vinylbenzyl alcohol;
ar-dihydroxybenzyl alcohol.

The oxidation process of this invention occurs when molecular oxygen or air is contacted with an aryl-substituted alcohol according to the previously described process. At the end of the reaction time, the noble metal catalyst is removed and the organic phase is separated from the aqueous phase. Evaporation of the organic solvent serves to isolate the crude aldehyde product. The crude aldehyde product may be purified by distillation, recrystallization, or other known methods.

The noble metal-containing oxidation catalysts that may be used in the practice of the invention include platinum, palladium, rhodium, iridium, ruthenium, osmium, and mixtures thereof. Preferred are platinum and palladium. The catalyst may be in various forms such as, for example, platinum black, palladium black, platinum oxide, palladium oxide, or the noble metal deposited on various supports such as charcoal, calcium carbonate, activated aluminas and silicas, or equivalent materials. To reduce the cost of the catalyst, the noble metal is generally deposited on an inert carrier, such as carbon, alumina, graphite, silica gel, barium sulfate, or calcium carbonate. Catalysts that contain from about 0.25 to 10 percent by weight of the noble metal on a carrier are particularly useful. The amount of the catalyst used is that which will cause the oxidation to take place at the desired rate; it is dependent upon such factors as the choice of aryl-substituted alcohol, the choice of organic solvent, the amount of organic solvent that is used, and the form of the catalyst. In a batch process the ratio of noble metal catalyst to alcohol is between 1:5 and 1:10 for optimum results.

Benefits may also be obtained by the addition of certain known additives or promoters to the noble metal catalyst. For example, in U.S. Pat. No. 4,119,671 it is taught that certain metal activators, specfically lead, silver, tellurium, and/or tin and/or compounds thereof may be added to considerably reduce the consumption of noble metal catalyst and the formation of tar deposits. It was found that such activators could be added in amounts from $1 \times 10^{-5}$ to $1 \times 10^{-1}$ mol per mol of hydroxymethyl group oxidized. The complete teaching of U.S. Pat. No. 4,119,671 is herein incorporated by reference.

Additional activating substances previously known in the prior art as useful to improve the performance of the noble metal catalysts used in this process include boric acids or borates, cadmium, cerium, indium, lanthanum, copper, yttrium, magnesium, uranium and zinc ions and bismuth-containing compounds. Such activating substances may also be employed according to the instant invention.

When an organic solvent is present, a catalytic amount of an alkali metal hydroxide or carbonate, as little as 0.1 mole for each mole of the aromatic alcohol, causes the oxidation reaction to proceed at a satisfactory, commercially attractive rate. The rate at which the aromatic alcohol is oxidized to the corresponding aldehyde can be increased by adding to the reaction mixture a larger than catalytic amount of the alkali metal hydroxide or carbonate. In most cases, about 0.3 to about 1.0 mole for each mole of the aromatic alcohol, is preferred.

The alkali metal hydroxides or carbonates that can be used in catalytic amounts in the noble metal catalyzed oxidation of aromatic alcohols are hydroxides or carbonates of sodium, potassium, cesium, lithium, rubidium, and francium. Potassium or sodium hydroxide are particularly well suited for this process.

The organic solvents suitable for this invention are those liquids that are solvents for the aldehyde reaction products formed and that additionally are immiscible in the aqueous phase and stable under the oxidation conditions employed. Preferably they are selected from the group consisting of hydrocarbons, chlorinated aliphatic and chlorinated aromatic hydrocarbons. Illustrative of these compounds are hexane, heptane, octane, nonane, benzene, methylene chloride, o-dichlorobenzene, perchloroethylene, and the like. Most preferred are chlorinated aliphatic and chlorinated aromatic hydrocarbons. The organic solvent and water are preferably used in approximately equal amounts.

In some embodiments, a batch process may be used which consists of bringing the organic solvent, the alcohol to be oxidized, the alkaline agent and the noble metal catalyst, into contact with molecular oxygen or a gas containing the latter. The process can be carried out at atmospheric pressure or superatmospheric pressure, as desired. The mixture is then stirred or otherwise agitated at the desired temperature to facilitate the oxidation process. After sufficient conversion of the alcohol to the corresponding aldehyde occurs, the noble metal catalyst is then removed by filtering and the organic phase is separated from the aqueous phase and the crude aldehyde product isolated.

The process may of course be operated in continuous manner. For example, a stream of oxygen or a gas containing oxygen may be passed into and through a treatment zone containing a fixed bed of the noble metal catalyst, concurrently with streams of the aqueous alkaline solution and the organic solvent along with the alcohol to be oxidized. Oxygenations conducted in this manner readily permit recycling of the aqueous alkaline medium and the efficient separation of the organic phase containing the desired product.

In general terms, the reaction is carried out in a temperature range extending from 25° C. to 130° C.; the preferred range depends on the boiling point of the solvent used; the reaction temperature should be maintained below the boiling point of the solvent of choice to prevent the loss of product.

The surprising and unexpected phenomenon that is the essence of this invention is the effect of the organic solvent. The addition of the organic solvent creates a two-phase liquid reaction medium comprising an inert, water-immiscible, organic liquid and water. The discovery that the process could be conducted in the presence of an organic solvent without deleteriously affecting the reaction rate was most surprising and when used in combination with the other reactants permits a greatly simplified method of oxidation whereby the requirement in prior art processes that the alkaline agent be neutralized is eliminated.

This invention is further illustrated by the following nonlimiting examples. In these examples, all parts and percentages are by weight unless otherwise specified.

EXAMPLE 1

In a 500 milliliter (ml) three-necked flask equipped with a high-speed agitator, a gas inlet tube, a thermometer, and a reflux condenser are placed 1.5 parts of sodium hydroxide, 80 parts of water, 2 parts of a 5 percent palladium-on-charcoal, 132 parts of methylene chloride and 20 parts of p-methoxybenzyl alcohol. A stream of air or oxygen is passed into the vapor space above the reaction mixture forming an oxygen blanket. The reaction mixture is stirred vigorously to permit sufficient diffusion of air into the mixture and is refluxed at 40° C. for a period of 6–7 hours. At the end of the reaction time, the palladium-on-charcoal catalyst is filtered out of the reaction mixture and the organic phase, consisting essentially of methylene chloride and aldehyde product, is separated with a separatory funnel. 18.0 Parts of crude p-methoxybenzaldehyde is recovered after the evaporation of the methylene chloride solvent. This represents a product yield of approximately 85 percent based on the starting amount of p-methoxybenzyl alcohol. A vapor phase chromatography (VPC) co-injection technique and comparison of the proton magnetic resonance (pmr) spectrum of a p-methoxybenzaldehyde standard are used to verify the identity of the aldehyde product.

EXAMPLE 2

In substantially the same manner as in Example 1, 0.16 part of sodium hydroxide, 60 parts of water, 3.2 parts of 5 percent palladium-on-charcoal, 264 parts of methylene chloride and 5 parts of o-hydroxybenzyl alcohol are stirred in the presence of air and refluxed at 45° C.–48° C. for approximately three hours; VPC analysis of the reaction mixture at 160° C. reveals aldehyde formation. The crude reaction mixture is filtered and separated as in Example 1. 2.01 Parts of o-hydroxybenzaldehyde are isolated; 1.49 parts of unreacted o-hydroxybenzyl alcohol are also recovered indicating the reaction had not gone to completion.

What is claimed is:

1. A process for the production of an aromatic aldehyde consisting essentially of the following steps:

(a) subjecting an aryl-substituted alcohol of the formula:

   Ar(—CH=CH—)$_n$CH$_2$OH wherein n is 0, 1 or 2, and Ar is an aromatic radical having at least one benzene ring, to the action of molecular oxygen in the presence of a noble metal catalyst in a two-phase liquid reaction medium consisting of an organic phase comprising an inert, water-immiscible organic liquid which is a solvent for the aromatic aldehyde produced, and an aqueous phase comprising an aqueous alkaline solution, at a temperature below the decomposition temperature of the alcohol;

(b) at the end of the reaction time, separating the organic phase from the aqueous phase, and isolating the resulting aldehyde from the organic phase; and (c) recycling the separated aqueous phase without neutralization for subsequent reuse as the aqueous phase in step (a).

2. The process of claim 1 wherein n is 0.

3. The process of claim 1 wherein the aryl-substituted alcohol is of the formula:

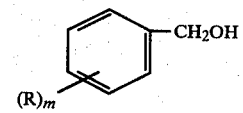

in which the —CH$_2$OH radical is in the ortho-, meta- or para-position relative to R, the R radicals are independently selected from OR', vinyl, nitro, halo, alkyl of 1 to 22 carbon atoms, alkenyl of 1 to 22 carbon atoms, R' is hydrogen, aryl, alkyl of 1 to 22 carbon atoms, and m is a whole number from 0 to 2.

4. The process of claim 1 wherein the organic liquid is selected from the group consisting of chlorinated aliphatic and chlorinated aromatic hydrocarbons.

5. The process of claim 4 wherein the noble metal catalyst is deposited on an inert support.

6. The process of claim 1 or 5 wherein the noble metal is platinum or palladium.

7. The process of claim 6 wherein the aqueous alkaline solution comprises an aqueous alkali metal hydroxide or alkali metal carbonate solution.

8. The process of claim 7 wherein the alcohol to be oxidized is para-methoxybenzyl alcohol.

9. The process of claim 7 wherein the alcohol to be oxidized is selected from the group consisting of ortho-, meta-, and para-hydroxybenzyl alcohol.

10. The process of claim 1 wherein the reaction medium additionally includes a catalyst activator.

* * * * *